US00PP30371P3

(12) United States Plant Patent
Skotak, Jr.

(10) Patent No.: US PP30,371 P3
(45) Date of Patent: Apr. 9, 2019

(54) *GUZMANIA* PLANT NAMED 'DURAMIA'

(50) Latin Name: ***Guzmania* hybrid**
Varietal Denomination: DURAMIA

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 0 days.

(21) Appl. No.: 15/732,217

(22) Filed: Oct. 4, 2017

(65) Prior Publication Data

US 2019/0029159 P1 Jan. 24, 2019

(30) Foreign Application Priority Data

Jul. 18, 2017 (QZ) ..... PBR 2017/1808

(51) Int. Cl.
*A01H 5/02* (2018.01)
*A01H 6/22* (2018.01)

(52) U.S. Cl.
USPC ..... Plt./371
CPC ..... *A01H 6/225* (2018.05)

(58) Field of Classification Search
USPC ..... Plt./371
See application file for complete search history.

*Primary Examiner* — Keith O. Robinson
(74) *Attorney, Agent, or Firm* — Samuel R. McCoy, Jr.

(57) ABSTRACT

A new and distinct variety of *Guzmania* plant named 'DURAMIA' which is characterized by the combination of a compact monopodial growth habit with foliage arranged in an attractive rosette, short and broad, dark green foliage, a compact inflorescence which is positioned below the foliage plane, a red and yellow bicolored inflorescence with a yellow center, and the stability of all characteristics from generation to generation.

3 Drawing Sheets

Latin name of the genus and species: The Latin name of the genus and species of the novel variety disclosed herein is *Guzmania* hybrid.

Variety denomination:

The inventive variety of *Guzmania* disclosed herein has been given the variety denomination 'DURAMIA'.

CROSS REFERENCE TO RELATED APPLICATIONS

This application claims priority to the Community Plant Variety Rights application number 2017/1808, filed Jul. 18, 2017, which is herein incorporated by reference.

BACKGROUND OF THE INVENTION

Parentage: The *Guzmania* variety 'DURAMIA' is an F1 hybrid seedling selection which resulted from a controlled pollination breeding program. In May of 2004, the inventor performed the controlled cross-pollination of *Guzmania* hybrid 'Depladia' (U.S. Plant Pat. No. 13,577), the seed parent, and *Guzmania lingulata* 'Magnifica' (not patented), the pollen parent, at a commercial greenhouse in Alajuela, Costa Rica. Those skilled in the art recognize that *Guzmania* seed can be difficult to germinate. Therefore, in September of 2004, the seed that resulted from the cross of May 2004 in Alajuela, Costa Rica were shipped by the inventor to a tissue culture laboratory in Evergem, Belgium for in vitro seed germination in order to increase the germination rate. At the direction of the inventor, the resulting seedlings were grown for 6 months to evaluate plant vigor and the most vigorous seedlings, given the population code 8222, were then shipped back to Alajuela, Costa Rica for further evaluation by the inventor. In May of 2007, the inventor selected one seedling for further evaluation due to its unique growth habit and flower characteristics, giving the seedling the experimental code, 8222#1. This seedling was further evaluated for several years in order to confirm the distinctness and stability of the characteristics first observed. Upon confirmation this new and distinctive cultivar was given the name 'DURAMIA'.

Asexual Reproduction: 'DURAMIA' was first asexually propagated by meristematic tissue culture in January of 2014 at a commercial laboratory in Evergem, Belgium and has since been asexually propagated through 3 additional generations. Through subsequent generations, the unique features of this cultivar are stable and reproduced true to type.

SUMMARY OF THE INVENTION

The cultivar 'DURAMIA' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'DURAMIA'. These characteristics, in combination, distinguish 'DURAMIA' as a new and distinct *Guzmania* cultivar:

1. *Guzmania* 'DURAMIA' exhibits a compact monopodial growth habit with foliage arranged in an attractive rosette; and
2. *Guzmania* 'DURAMIA' exhibits short and broad, dark green foliage; and
3. *Guzmania* 'DURAMIA' exhibits a compact inflorescence which is positioned below the foliage plane; and 4. *Guzmania* 'DURAMIA' exhibits a red and yellow bicolored inflorescence with a yellow center.

BOTANICAL DESCRIPTION OF THE PLANT

Figure 1:
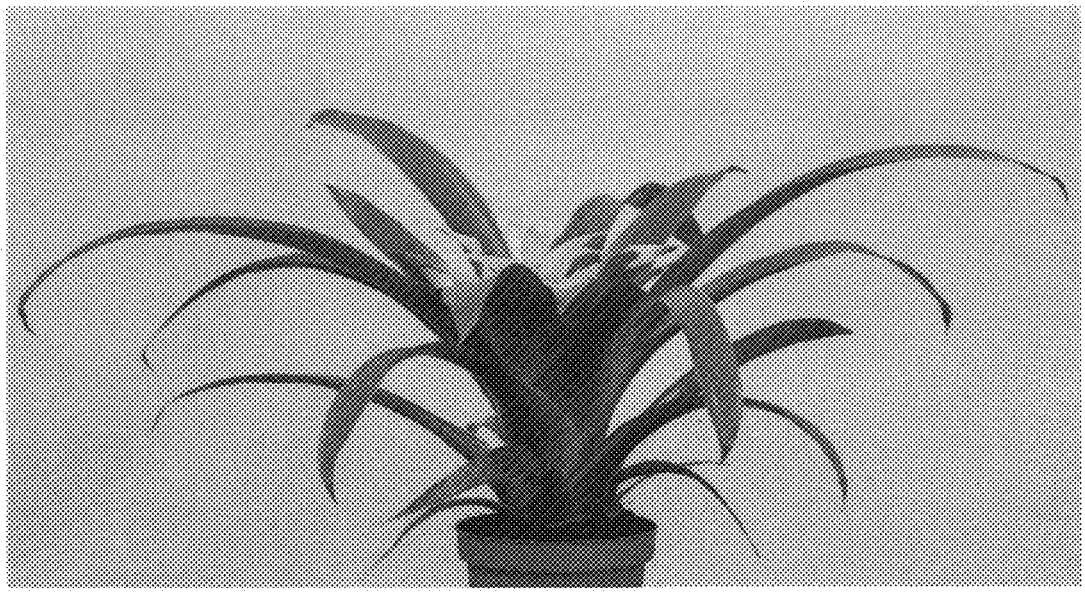
FIG. 1 illustrates, as nearly true as it is reasonably possible to make the same in color photographs of this type, an exemplary plant of 'DURAMIA' grown in a commercial greenhouse in Evergem, Belgium. This plant is approximately 18 month old, shown planted in a 9 cm container.
Figure 2:
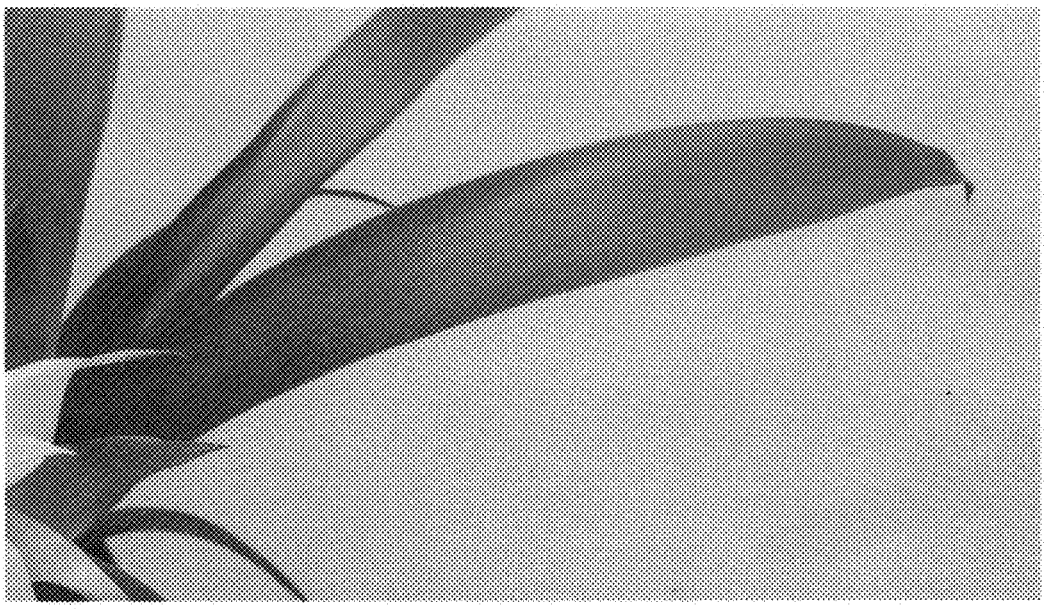
FIG. 2 illustrates, as nearly true as it is reasonably possible to make the same in color photographs of this type, the typical foliage of 'DURAMIA'
Figure 3:
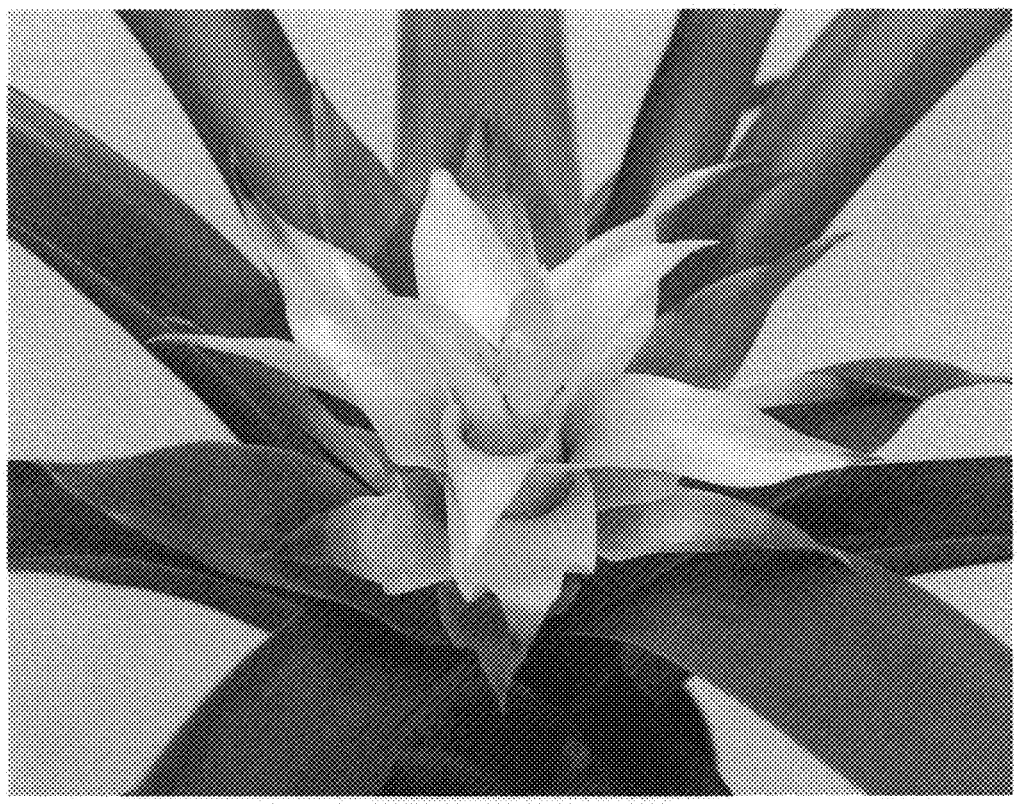
FIG. 3 illustrates, as nearly true as it is reasonably possible to make the same in color photographs of this type, the typical inflorescence of 'DURAMIA'.

The following observations and measurements made in August of 2017 describe averages from a sample set of six specimens of 18 month-old 'DURAMIA' plants grown in 9 cm nursery pots at a commercial greenhouse in Evergem, Belgium. Plants were grown under light maximum light levels of approximately 12,000 lux. Plants were maintained with a fertigation program and regularly watered with overhead irrigation. No chemical pest measures were taken.

Those skilled in the art will appreciate that certain characteristics will vary with older or, conversely, with younger plants. 'DURAMIA' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 2015 (sixth edition).

A botanical description of 'DURAMIA' and a comparison with the parent plants and most similar variety of *Guzmania* are provided below.

Plant description:

*Growth habit.*—Perennial; monopodial; broad, upright. Leaves arranged in a basal rosette, with no lateral branching, and the inflorescence growing from the center of the basal rosette.

*Plant form.*—Flattened globular.

*Average height.*—17.3 cm, from the soil level to the top of the foliar plane, and 14.1 to the top of the floral plane.

*Plant spread.*—Average of 41.5 cm.

*Growth rate.*—Low.

*Plant vigor.*—Low to moderate.

*Propagation type.*—Mericloning.

*Time to initiate roots.*—Approximately 14 days to initiate roots at 22 degrees Celsius.

*Time to produce a finished plant.*—Approximately 18 months are needed to produce a marketable plant in a 9 cm container.

*Pest resistance and susceptibility.*—Neither resistance nor susceptibility to typical *Guzmania* pests and diseases has been observed.

*Temperature tolerances.*—USDA Zones 10 to 12; at least tolerant of temperatures to 40 degrees Celsius. High tolerance to rain inundation; high tolerance to wind.

Root system:

*General.*—Thick; medium density.

*Texture.*—Slightly fleshy.

Foliage:

*Arrangement.*—Rosulate. No stems or lateral branches, the leaves form a stem-like structure not consisting of a stem as such, but only consisting of the leaf sheaths.

*Attachment.*—Sheathed.

*Division.*—Simple.

*Quantity of leaves.*—17.

*Lamina.*—Dimensions — 29.9 cm long and 2.9 cm wide. Thickness — Approximately 0.9 cm. Shape of blade — Ensiform. Aspect — Concave. Attitude — Moderately reflexed. Apex — Apiculate. Base — Sheathing. Margin — Entire; not undulated. Pubescence, texture and luster of adaxial surface — Glabrous, smooth and moderately glossy. Pubescence, texture and luster of abaxial surface — Glabrous, smooth and moderately glossy. Color — Juvenile foliage, adaxial surface — Yellow-green, nearest to in between RHS 144A and 146A. Juvenile foliage, abaxial surface — Yellow-green, nearest to RHS 146A. Mature foliage, adaxial surface — Green to yellow-green, in between RHS 137A and 146A. Mature foliage, abaxial surface — Green, nearest to RHS 137B. Venation — Pattern — Parallel. Mature foliage venation, adaxial surface — Green to yellow-green, in between RHS 137A and 146A. Mature foliage venation, abaxial surface — Green, nearest to RHS 137B.

*Sheath.*—Sheath length — Average 10.0 cm. Sheath width — Average 6.0 cm. Sheath color — Greyed-yellow, nearest to RHS 162D, and darker towards the base, nearest to RHS 161C.

Inflorescence:

*Inflorescence arrangement.*—Terminal spike with showy bracts and an average of 15 flowers.

*Natural flowering season.*—Continuously.

*Time to flower.*—Approximately 6 months.

*Inflorescence quantity.*—One.

*Flowers per inflorescence.*—Average of 15, with 8 open flower and 7 in bud stage and not opening.

*Inflorescence height.*—Approximately 7.5 cm (measured from base of lowest flower to top of upper flower).

*Inflorescence diameter.*—Average of 2.0 cm, excluding bracts, and 13.2 cm with bracts.

*Peduncle.*—Dimensions — Approximately 8.5 cm long and 0.9 cm in diameter. Aspect — Near horizontal. Strength — Strong. Texture and luster — Glabrous, smooth, and glossy. Color — White, RHS NN155A.

Bud:

*Length.*—Average of 1.4 cm.

*Diameter.*—Average of 0.35 cm.

*Shape.*—Narrow oblong.

*Texture and luster.*—Glabrous, smooth, and moderately glossy.

*Color.*—Yellow, nearest to RHS 5B; base is white, nearest to RHS NN155D.

Flower:

*Flower type and form.*—Single; oblanceolate to narrow oblong.

*Attachment.*—Sessile.

*Aspect.*—Vertical.

*Flowering habit.*—Freely flowering; continuous.

*Height.*—Approximately 0.2 cm.

*Diameter.*—Average of 0.4 cm.

*Depth.*—Approximately 2.0 cm.

*Floral throat diameter.*—0.2 cm.

*Floral throat texture.*—Glabrous; smooth.

*Diameter of floral tube.*—0.2 cm.

*Length of floral tube.*—1.5 cm.

*Floral tube texture, outer and inner surfaces.*—Glabrous; smooth.

*Fragrance.*—No fragrance.

*Lastingness.*—4 weeks.

*Persistent.*—Persistent.

*Petals.*—Quantity of Petals — 3. Arrangement — Rotate; single whorl of fused petals with the proximal 75% of the petals fused. Length — Approximately 2.0 cm. Width — Approximately 0.3 cm. Shape — Narrow oblong; concave. Apex — Obtuse. Base — Fused into a tube. Margin — Entire; not undulated. Pubescence, texture and luster of upper surface — Glabrous, smooth and very slightly glossy. Pubescence, texture and luster of lower surface — Glabrous, smooth and very moderately glossy. Color when opening, upper surface — Yellow, nearest to RHS 7A; apex is white, nearest to RHS NN155B. Color when opening, lower surface — Yellow, nearest to RHS 7A; apex is white, nearest to RHS NN155B. Color when fully opened, upper surface — Yellow, nearest to RHS 7A; apex is white, nearest to RHS NN155B. Color when fully opened, lower surface — Yellow, nearest to RHS 7A; apex is white, nearest to RHS NN155B. Fading, upper surface — Not fading. Fading, lower surface — Not fading. Venation color, fully opened, upper surface — No venation is visible. Venation color, fully opened, lower surface — No venation is visible. Floral throat color — Yellow, nearest to RHS 7A. Floral throat venation color — No venation is visible. Floral tube color, when fully opened — Yellow, nearest to RHS 7A. Floral tube venation color — No venation is visible.

*Calyx.*—Shape — Rotate. Length — Average of 1.7 cm. Diameter — Average of 0.6 cm.

*Sepals.*—Quantity — 3 unfused sepals in a single whorl. Arrangement — Rotate. Length — 2.2 cm. Width — 0.3 cm. Shape — Lanceolate; strongly concave. Apex — Acute. Base — Cuneate. Margin — Entire. Pubescence, texture and luster of upper surface — Glabrous, smooth, and slightly glossy. Pubescence, texture and luster of lower surface — Glabrous, smooth, and slightly glossy. Color when opening, upper surface — Yellow, nearest to RHS 8C, and fading to white towards the base, nearest to RHS 155A. Color when opening, lower surface — Yellow, nearest to RHS 8C, and fading to white towards the base, nearest to RHS 155A. Color when fully opened, upper surface — Yellow, nearest to RHS 8C, and fading to white towards the base, nearest to RHS 155A. Color when fully opened, lower surface — Yellow, nearest to RHS 8C, and fading to white towards the base, nearest to RHS 155A.

*Bract.*—General — One large, colorful bract at the base of each individual flower. Quantity — Average of 15. Shape — Obovate to oblong; concave. Dimensions — Average of 8.4 cm long, including the sheath, and 2.5 cm wide. Apex — Acute. Base — Sheathing. Margins — Entire. Texture and luster, upper surface — Smooth and moderately glossy. Texture and luster, lower surface — Smooth and slightly glossy. Upper bract color, upper surface — Yellow, nearest to RHS 13A. Upper bract color, lower surface — Yellow, nearest to RHS 13B. Lower bract color, upper surface — Yellow, nearest to RHS 13A; orange-red towards the apex, nearest to RHS N34D, and tipped greyed-purple, nearest to RHS N186C. Lower bract color, lower surface — Yellow, nearest to RHS 13B; orange-red towards the apex, nearest to RHS N34D, and tipped yellow-green, nearest to RHS 146A. Peduncle bracts, upper surface — Yellow-green, nearest to in between RHS 150B and 150C; middle section is suffused with orange-red, nearest to RHS 34C; apex is green, nearest to RHS 137B. Peduncle bracts, lower surface — Yellow-green, nearest to RHS 150C; middle section is suffused with orange-red, nearest to RHS 34C; apex is yellow-green, nearest to in between RHS 146B and 147B. Sheath — Sheath length — Average 2.9 cm. Sheath width — Average 3.9 cm. Sheath color, upper surface — Greyed-yellow; nearest to RHS 160D. Sheath color, lower surface — Greyed-yellow; nearest to RHS 160D. Venation — No venation is visible.

Reproductive organs:

*Stamens.*—Quantity — 6, on average. Anthers — Shape — Dorsifixed; narrow sagitate. Dimensions — Average of 0.5 cm long and 0.05 cm wide. Color — Yellow, nearest to RHS 11D. Filaments — Length — 0.2 cm, on average. Color — Yellow, nearest to RHS 11B. Pollen — None detected.

*Pistil.*—Quantity — 1. Length — 0.6 cm. Style — Length — 0.5 cm. Color — Yellow, nearest to in between RHS 4B and 4C. Stigma — Shape — Club-shaped. Dimensions — Average of 0.1 cm long and 0.1 cm wide. Color — Yellow, nearest to RHS 4D. Ovary Color — Yellow-green, nearest to RHS 150D.

Fruit and seed: To date, not observed.

COMPARISONS WITH THE PARENT PLANT

Plants of the new cultivar 'DURAMIA' differ from its seed parent, *Guzmania* hybrid 'Depladia' (U.S. Plant Pat. No. 13,577), by the characteristics described in Chart 1.

CHART 1

| Characteristic | 'DURAMIA' | 'Depladia' |
|---|---|---|
| General coloration of the bracts. | Red and yellow. | Yellow. |
| Inflorescence height. | Short; compaact. | Tall; elongated. |

Plants of the new cultivar 'DURAMIA' differ from its pollen parent, *Guzmania lingulata* 'Magnifica' (not patented), by the characteristics described in Chart 2.

CHART 2

| Characteristic | 'DURAMIA' | 'Magnifica' |
|---|---|---|
| General coloration of the bracts. | Red and yellow. | Yellow. |
| Inflorescence height. | Short; compact. | Tall; elongated. |

COMPARISON WITH THE MOST SIMILAR *GUZMANIA* CULTIVAR KNOWN TO THE INVENTOR

'DURAMIA' is similar in many horticultural characteristics to the commercial cultivar *Guzmania* 'Fancy' (not patented). However 'DURAMIA' differs from 'Fancy' by the characteristics described in Chart 3.

CHART 3

| Characteristic | 'DURAMIA' | 'Fancy' |
|---|---|---|
| Length of foliage. | Short. | Long. |
| General coloration of the foliage. | Green. | Darker green. |
| Inflorescence height. | Short; compact. | Tall; elongated. |

That which is claimed is:

1. A new and distinct variety of *Guzmania* plant named 'DURAMIA', substantially as described and illustrated herein.

* * * * *